United States Patent [19]

Oneto et al.

[11] 4,130,497
[45] Dec. 19, 1978

[54] DETERGENT COMPOSITION

[75] Inventors: Francis E. J. Oneto, Clichy-sous-Bois; André J. E. Benzoni, Livry-Gargan; Jacques L. Poret, Mitry-Mory; Fernand B. Simon, Margency, all of France

[73] Assignee: Lever Brothers Company, New York, N.Y.

[21] Appl. No.: 758,819

[22] Filed: Jan. 12, 1977

[30] Foreign Application Priority Data

Jan. 16, 1976 [GB] United Kingdom ............... 1793/76

[51] Int. Cl.$^2$ ............................................. C11D 1/10
[52] U.S. Cl. .......................... 252/89 R; 252/DIG. 5; 252/DIG. 13; 252/DIG. 14; 252/132; 424/70; 424/365
[58] Field of Search ................ 252/DIG. 5, DIG. 13, 252/89 R, 551, 132, 108, DIG. 14; 424/70, 365

[56] References Cited

U.S. PATENT DOCUMENTS

| 3,943,234 | 3/1976 | Roggenkamp | 252/DIG. 5 |
| 4,026,825 | 5/1977 | Steen et al. | 252/551 |

OTHER PUBLICATIONS

McCutcheon's "Detergents & Emulsifiers", 1976 Annual, McCutcheon's Division Publishing Co., p. 3.

*Primary Examiner*—George F. Lesmes
*Assistant Examiner*—Edith R. Buffalon
*Attorney, Agent, or Firm*—Kenneth F. Dusyn; James J. Farrell; Melvin H. Kurtz

[57] ABSTRACT

A single liquid phase detergent composition, such as a foam bath product, contains a cosmetically acceptable oil as a skin benefit agent and a mixture of anhydrous anionic detergents. In use, when diluted in water, the composition is capable of producing and maintaining a substantial head of foam and is capable of depositing on the skin after immersion a noticeable amount of the oil.

8 Claims, No Drawings

DETERGENT COMPOSITION

The invention relates to foam bath compositions adapted to be added to bath water or for use when showering, also provide a film of a skin benefit agent on the skin which is retained after emerging from the bath or shower.

Some bath products for addition to bath water leave a film of oil on the skin. Generally, these products comprise an oil which tends to float on the surface of the bath water, which can interfere with the lathering of soap and which may leave a deposit of scum around the bath above the waterline which is inconvenient to remove after the bath water has drained away.

Some other bath products comprise a foam-producing surface active agent which when added to bath water with agitation can produce copious foam; such products generally reduce the problem of scum formation.

Whereas it is possible to prepare bath products containing both oil and foaming detergents, it is generally believed that foaming is inhibited by the presence of the oil and therefore these two components of the product are non-compatible. It has also been recognized that products of this type containing a detergent and an oil will tend to separate on standing so that the bath product will generally consist of two liquid phases which will require mixing thoroughly before dispensing in the bath water in order to ensure addition of the correct proportion of each phase.

Contrary to expectation, we have now discovered that it is possible to employ a special detergent together with an oil as a skin benefit ingredient which in admixture provides a single liquid phase product which does not partition on standing and which can be transparent. The product is adapted for addition to bath water to yield a copious foam which is stable in the presence of the oil and which provides a film of the oil which is retained on the skin after emerging from the bath.

Accordingly the invention provides a single liquid phase detergent composition comprising:
(i) from 15 to 50% by weight of a cosmetically acceptable oil; and
(ii) from 40 to 75% by weight of an anionic detergent mixture comprising
  (a) an anhydrous amine salt of a $C_8$ to $C_{18}$ fatty alcohol sulphate containing an average of from 0 to 4 moles of ethylene oxide; and
  (b) an anhydrous alkyl or alkylaryl substituted ethoxylated oxacarboxylic acid or a sodium or an amine salt thereof having the empirical formula:

$$R.(OCH_2CH_2)_n.OCH_2COOX$$

where
R is $C_8$ to $C_{18}$ alkyl or $C_6$ to $C_{12}$ alkylphenyl;
n has an average value of from 1 to 15; and
x is hydrogen sodium or an amine residue.

The oil which forms the oily skin benefit ingredient of the composition is cosmetically acceptable and nonirritant, and is preferably a triglyceride in which the medium chain $C_8$ to $C_{12}$ triglycerides predominate. As an alternative, mineral oils such as paraffin oil, can be used as oily skin benefit ingredients. It is also possible to use a mixture of two or more oils.

Although the quantity of the oil employed is by weight from 15 to 50%, it is preferable to use from 20 to 40%, most preferably 25 to 35% by weight of the detergent composition.

Use of less than 15% by weight of the oil is unlikely in use to provide the bather with a noticeable skin benefit, whereas use of more than 50% by weight can cause the product to partition on standing and can in use deposit on the skin of the bather an excessive amount of the oil, thus leaving the skin too greasy. Furthermore, the foaming ability of the composition can be depressed.

The special anionic detergent mixture which forms an essential part of the composition according to the invention is preferably anhydrous and is an anionic detergent comprising a mixture of two components. The first is an anhydrous amine salt of a $C_8$ to $C_{18}$ fatty alcohol sulphate containing an average of from 0 to 4 moles of ethylene oxide.

Preferred examples of the first anionic detergent are mono- or di-ethyl ethanolamine salts of lauryl ether sulphate having an average of 2 to 3 moles of ethylene oxide; diethylamine and monobutylethanolamine salts of lauryl ether sulphate and the corresponding amine salts of nonyl penyl and octylphenyl sulphate.

The second anionic detergent is an anhydrous alkyl or alkylaryl substituted ethoxylated oxacarboxylic acid or a sodium or an amine salt thereof having the empirical formula:

$$R.(OCH_2CH_2)_n.OCH_2COOX$$

where R is $C_8$ to $C_{18}$ alkyl to $C_6$ to $C_{12}$ alkyl-phenyl;
n has an average value of from 1 to 15; and
X is hydrogen, sodium or an amine residue.

Preferred examples of the second anionic detergent are those having an average of 4 to 5 moles ethylene oxide such as lauryl (poly-1-oxapropene) oxaethane carboxylic acid, nonyl-phenyl (poly-1-oxapropene) oxaethane carboxylic acid, and their corresponding monoethanolamine salts.

The anionic detergent mixture employed functions both to provide a copious foam when mixed and agitated with water and also to maintain the oil component in solution in the composition before dilution by adding it to bath water or before use when showering. By this means, the composition retains its usually clear transparent character and does not partition on standing into two or more phases at the normal temperature of storage which is usually from 5° to 20°.

Although the quantity of the anionic detergent mixture employed is by weight from 40 to 75% of the composition, it is preferable to use from 45 to 50% by weight of this mixture.

Use of less than 40% by weight of detergent mixture of detergents is unlikely in use to provide the bather with sufficient foam when the composition is diluted with agitation in bath water and also it cannot be guaranteed that the composition containing the oil ingredient will remain as a single liquid phase. It has also been noted that if more than 75% by weight of the total detergent mixture is present in the composition then the foam can be too copious, a property which might persuade the user to employ less of the composition in the bath water than is necessary to provide a noticeable skin benefit from deposition of the oil on the skin of the bather. Furthermore, an excessive concentration of the detergent mixture, even after dilution in use, might lead to irritation or other skin damage.

For optimum results, we have found that within the stated limits for the total anionic detergent content of the composition, the weight ratio of the sulphated alcohol to the substituted carboxylic acid or its sodium or amine salt should be from 1:1.5 to 1:8, preferably, from 1:2 to 1:4 and ideally about 1:3. It follows that the detergent composition according to the invention will normally contain from 4 to 30% by weight of the sulphated alcohol and from 24 to 67% by weight of the substituted oxacarboxylic acid or its sodium or amine salt.

According to a particularly preferred formulation, the composition contained by weight 12% of the sulphated alcohol and 35% of a substituted oxa carboxylic acid making a total of 47% anionic detergent by weight of the composition.

It should be noted that compositions according to the invention are usually substantially free from added water. This is to ensure that the composition is normally in the form of a single liquid phase before dilution by addition to bath water. However, it is optionally possible to incorporate up to 5% by weight of water in these compositions, for example, to aid solubilization of a colorant.

In addition to the skin benefit oil ingredient and the anionic detergent mixture, it is also possible to incorporate in the composition other ingredients such as thickeners, foam boosters, foam stabilizers, coloring matter, perfumes and preservatives, the amounts of such additive materials being similar to those which are usually employed in bath or shower products.

When required for use, the composition can be diluted as required by the user, but as a guide, we have found that addition of 30g of the composition with agitation to a total of 100 liters of bath water, giving a dilution of the composition to about 0.3g/l, is ideal for providing a copious foam and for depositing a clearly noticeable film of the skin benefit oil on the skin of the bather. As a further guide, it is apparent that a dilution of the composition in water of from 0.1 to 0.5g/l is preferred.

It should be explained that reference herein to the ability of detergent compositions according to the invention to produce a "copious foam" when mixed with bath water means that they satisfy a laboratory test for foam production which can be carried out under standard conditions as follows.

Test for the Determination of the Foaming Power of a Detergent Composition

A 3g sample of a detergent composition to be tested is placed in a graduated glass tank of rectangular cross section 200 mm wide × 600 mm long × 400 mm deep. The tank is fitted with an overhead sparger tube resting on the top edges of the tank, the sparger being drilled with 24 holes each 0.9 mm in diameter and spaced 16 mm apart along the length of the tank.

At the commencement of the test, water at a temperature of 37° C. and having a degree of hardness of 30° (French) is admitted to the tank via the sparger holes at a flow rate of 4.4 l/min via a standard metering pump until the total volume of water admitted is 10 liters. The foam height in mm above the water level is then read immediately and it is this figure which is used to assess the foaming power of the test sample of the detergent composition.

A sample which is capable of producing under these conditions a foam height of 20 mm or more is said to be capable of producing a copious foam.

Preferred detergent compositions according to the invention are those which are capable of producing a foam height of at least 40 mm and the best compositions are capable of producing a foam height of at least 50 mm.

Reference has also been made to the deposition and retention on the skin of the skin benefit ingredient of the detergent composition. This is usually discernible as a pleasantly smooth or supple feeling which is imparted to the skin after having been immersed in the foaming bath water and after removal of surplus water, for example with a towel. It is appreciated however that the reaction between individuals will vary because of the subjective nature of their appreciation of the deposited skin benefit ingredient. Accordingly, a test for measuring objectively the amount of skin benefit ingredient which is actually retained by the skin has been devised. In this test to be described later, a conventional solvent extraction technique is employed in which adsorption of the skin benefit oil on living human skin is measured after extraction with a suitable solvent. By this means it is possible to judge the ability of the detergent composition in use to deposit the skin benefit ingredient on the skin.

Although, as has been indicated, it is difficult to assay subjectively the amount of oil deposited on and retained by the skin, a clinical method for comparing the effect of detergent compositions according to the invention with those of the detergent compositions, has been devised. This method which employs a panel of trained assessors who score the skin condition of a group of persons before and after treatment with test and control compositions, is described in detail later.

The detergent compositions according to the invention are preferably transparent and are usually formulated for use as foam bath products, but as we have indicated, they can also be formulated to provide products for use when showering, such as shower gels. As a further alternative the detergent compositions can be shampoo products.

The invention also provides a process for the production of a single liquid phase detergent composition which is characterized by the steps of:
(i) blending together a first anhydrous anionic detergent comprising
  (a) an anhydrous amine salt of a $C_8$ to $C_{18}$ fatty alcohol sulphate containing an average of from 0 to 4 moles of ethylene oxide; with a second anhydrous anionic detergent comprising
  (b) an anhydrous alkyl or alkylaryl substituted ethoxylated oxacarboxylic acid or a sodium or an amine salt thereof having the empirical formula:

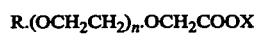

$$R.(OCH_2CH_2)_n.OCH_2COOX$$

where R is $C_8$ to $C_{18}$ alkyl or $C_6$ to $C_{12}$ alkylphenyl
  n has an average value of from 1 to 15; and
  x is hydrogen, sodium or an amine residue.
to provide an anionic detergent mixture,
(ii) dissolving a cosmetically acceptable oil in the anionic detergent mixture so formed; the amount of the anionic detergent mixture before dilution forming from 40 to 75% by weight of the composition, and the amount of the oil forming from 15 to 50% by weight of the composition, the composition so produced forming a single liquid phase.

The invention is illustrated by the following Examples.

EXAMPLE 1

A skin benefit foam bath composition was prepared by mixing together the following ingredients:

| | % w/w |
|---|---|
| AKYPO RLM 45 [Lauryl (poly-1-oxapropene) oxaethane carboxylic acid (90% AD)] | 35 |
| AKYPOSAL 100 LFS [Diethylamine and monobutylethaneolamine salt of lauryl ether sulphate ($C_{12}/C_{14}$ 70/30; 2.2 $\overline{EO}$) (100% AD)] | 12 |
| MYGLIOL 812 [Triglyceride $C_8$–$C_{12}$ fatty acids] | 35 |
| GENAGEN CA 050 [Ethoxylated (5EO) copra monoethanolamide] | 8 |
| STEINAMID DC 212S [Copra diethanolamide] | 5 |
| Perfume, color | 5 |

The foaming power height as measured by the test as described herein was 30 mm.

EXPERIMENT 1

An experiment was conducted using the skin benefit foam bath composition of Example 1 to illustrate the method employed for measuring the deposition of oil on the skin after treatment with the detergent composition.

A panel of human subjects was employed each of whom was asked to immerse a forearm in a bath containing the skin benefit foam bath composition of Example 1 diluted to 0.25g/l. After removal and drying of forearm, areas of 7 cm² were extracted with carbontetrachloride using 3 cm diameter crystallizing dishes filled with this solvent. The fatty material extracted included lipids normally present on the skin as well as oil freshly deposited from the foam bath.

Control extractions were carried out on the skin of the untreated forearms of each subject to provide a value for this natural skin lipid.

The total quantity of lipid present in each extract was determined by infra-red spectrophotometry of the methylene groups present in the extracted triglycerides. By difference, the amount of deposited oil was determined in this experiment as 5.8 μg/cm² of skin.

EXPERIMENT 2

In a further experiment, the skin benefit foam bath composition of Example 1 was compared with a commercially available foam bath product, as a control, the comparison being on the basis of subjective assessments by a panel of trained assessors who judged the skin condition of a group of subjects before and after treatment with each product.

The experiment was carried out as follows.

A group of 15 subjects were asked to immerse the forearm and hand of each arm (according to a statistical design) in a trough containing either the test or the control product diluted to a concentration of 0.25g/l at a temperature of 35°–38° C. Immersion took place for 15 minutes daily, five days a week for four weeks.

The skin of the hands and elbows of each subject was assessed at the beginning and the end of the experiment, the appearance and feel of the skin being scored according to the following hedonic scale:

0: skin nice and soft
1: skin slightly dry
2: skin dry
3: skin very dry
4 : skin very dry, slightly cornified
5 : skin very dry, cornified The test composition used was as described above under Example 1.

The control composition used was a commercially available foam bath product which has the following formulation:

| | |
|---|---|
| Sodium lauryl ether sulphate (3EO) 28% AD | 60 |
| Foam stabiliser | 2 |
| AUBYGUM SD (depolymeres seaweed extracts) | 0.9 |
| Perfume, color, water | to 100 |

The results of the subjective assessment were as follows:

| | Control | Test (Example 1) |
|---|---|---|
| Δmean score (DUNCAN test) | −0.40 | +0.30 |
| General comment | Slight deterioration in skin condition | Slight improvement in skin condition |

The results were subjected to a statistical analysis of variance as summarized in the Table below.

Table 1

| | Analysis of variance | | | | |
|---|---|---|---|---|---|
| | Degrees of freedom | Sum of squares | Mean square | F value | |
| Treatments | 1 | 10.13 | 10.13 | 7.39 | P<0.05 |
| Assessors | 1 | 2.68 | 2.68 | 1.96 | Not significant |
| Area (hand versus elbow) | 1 | 0.96 | 0.96 | 0.70 | Not significant |
| Subjects | 20 | 45.14 | 2.26 | 1.65 | Not significant |
| Error | 60 | 81.98 | 1.37 | | |

The conclusions of this analysis show that
(i) the test and control treatments were significantly different at P<0.05;
(ii) there was no significant different between the two assessors;
(iii) there was no significant difference between the two areas treated;
(iv) there was no significant difference between the scores derived from the 21 subjects, thus indicating that the panel was suitably chosen.

In conclusion, it was evident that the Test sample result for either the skin of the hand or the skin of the elbow was statistically significantly better than that of the Control, indicating the skin benefit of the oil.

EXAMPLE 2

A skin benefit foam bath composition was prepared by mixing together the following ingredients:

| | % w/w |
|---|---|
| AKYPO RLM 45 | 35 |
| AKYPOSAL 100 LFS | 12 |
| Paraffin oil | 35 |
| GENAGEN CA 050 | 8 |
| STEINAMID DC 2125 | 5 |
| Perfume, color | 5 |

The foaming power height was 50 mm.

The compositions of both Examples 1 and 2 consisted of a single transparent liquid phase and could be diluted to a concentration of 0.25 g/l of bath water to provide with agitation a copious foam and to deposit on the skin of the bather a noticeable film of skin benefit oil.

Each of the products described in the foregoing Examples developed a foam height in excess of 20 mm when subjected to the foaming power test as described hereinbefore.

What is claimed is:

1. A single liquid phase detergent composition comprising:
   (i) from 15 to 50% by weight of a cosmetically acceptable oil;
   (ii) from 40 to 75% by weight of an anionic detergent mixture comprising
      (a) an anhydrous amine salt of a $C_8$ to $C_{18}$ fatty alcohol sulphate containing an average of from 0 to 4 moles of ethylene oxide; and
      (b) an anhydrous alkyl or alkylaryl substituted ethoxylated oxacarboxylic acid or a sodium or an amine salt thereof having the empirical formula:

$$R-(OCH_2CH_2)_n-OCH_2COOX$$

where
      R is $C_8$ to $C_{18}$ alkyl or $C_6$ to $C_{12}$ alkylphenyl;
      n has an average value of from 1 to 15; and
      X is hydrogen, sodium or an amine residue; and
   (iii) from 0 to 5% water.

2. A composition according to claim 1, wherein the oil comprises a $C_8$ to $C_{12}$ triglyceride.

3. A composition according to claim 1, wherein the oil comprises paraffin oil.

4. A composition according to claim 1, wherein one component of the anionic detergent mixture is selected from the group consisting of mono- and di-ethyl ethanolamine salts of lauryl ether sulphate having an average of 2 to 3 moles of ethylene oxide; diethylamine and monobutylethanolamine salts of lauryl ether sulphate and the corresponding amine salts of nonylphenyl and octylphenyl sulphate and mixtures thereof.

5. A composition according to claim 1, wherein one component of the anionic detergent mixture is selected from the group consisting of lauryl (poly-1-oxapropene) oxaethane carboxylic acid, nonylphenyl (poly-1-oxapropene) oxaethane carboxylic acid, and their corresponding monoethanol amine salts and mixtures thereof.

6. A composition according to claim 1, which is in the form of a liquid foam bath composition.

7. A composition according to claim 1, which is in the form of a shower gel composition.

8. A process for the production of a composition according to claim 1, which process comprises:
   (i) blending together a first anhydrous anionic detergent comprising
      (a) an anhydrous amine salt of a $C_8$ to $C_{18}$ fatty alcohol sulphate containing an average of from 0 to 4 moles of ethylene, and a second anhydrous anionic detergent selected from the group consisting of
      (b) an anhydrous alkyl substituted ethoxylated oxacarboxylic acid, an anhydrous alkylaryl substituted ethoxylated oxacarboxylic acid, and their sodium and amine salts thereof, having the empirical formula:

$$R-(OCH_2CH_2)_n-OCH_2COOX$$

where
      R is $C_8$ to $C_{18}$ alkyl or $C_6$ to $C_{12}$ alkylphenyl;
      n has an average value of from 1 to 15; and
      x is hydrogen, sodium, or an amine residue to provide an anionic detergent mixture,
   (ii) dissolving a cosmetically acceptable oil in the anionic detergent mixture so formed; the amount of the anionic detergent mixture before dilution forming from 40 to 75% by weight of the composition, and the amount of the oil forming from 15 to 50% by weight of the composition, the composition so produced forming a single liquid phase.

* * * * *